United States Patent
Albin, Jr.

(10) Patent No.: US 7,430,912 B2
(45) Date of Patent: Oct. 7, 2008

(54) RANDOM INCIDENT ABSORBER APPROXIMATION

(75) Inventor: Donald C. Albin, Jr., Carlisle, PA (US)

(73) Assignee: International Automotive Components Group North America, Inc., Dearborn, MI (US)

( * ) Notice: Subject to any disclaimer, the term of this patent is extended or adjusted under 35 U.S.C. 154(b) by 478 days.

(21) Appl. No.: 11/275,358

(22) Filed: Dec. 28, 2005

(65) Prior Publication Data

US 2008/0083279 A1    Apr. 10, 2008

(51) Int. Cl.
*G01N 29/46* (2006.01)
*G01N 29/11* (2006.01)
*G01N 37/00* (2006.01)

(52) U.S. Cl. ............... 73/599; 73/865.6; 73/866
(58) Field of Classification Search ........ 73/571
See application file for complete search history.

(56) References Cited

U.S. PATENT DOCUMENTS

| | | | |
|---|---|---|---|
| 2,755,662 A * | 7/1956 | Swengel ............... | 73/599 |
| 3,346,067 A * | 10/1967 | Schroeder ............. | 73/599 |
| 4,242,398 A | 12/1980 | Segawa et al. | |
| 4,420,526 A | 12/1983 | Schilling et al. | |
| 4,828,910 A | 5/1989 | Haussling | |
| 5,068,001 A | 11/1991 | Haussling | |
| 6,526,840 B1 * | 3/2003 | Sakai et al. .......... | 73/865.6 |
| 6,541,105 B1 | 4/2003 | Park | |
| 6,667,254 B1 | 12/2003 | Thompson, Jr. et al. | |
| 6,820,923 B1 | 11/2004 | Bock | |
| 2001/0036970 A1 | 11/2001 | Park | |
| 2003/0062739 A1 | 4/2003 | Bock | |
| 2003/0077969 A1 | 4/2003 | Tanaka | |
| 2004/0050619 A1 | 3/2004 | Bargo, II | |
| 2004/0113309 A1 | 6/2004 | Thompson, Jr. et al. | |
| 2004/0131836 A1 | 7/2004 | Thompson | |
| 2005/0158536 A1 | 7/2005 | Tokoro et al. | |
| 2005/0178489 A1 * | 8/2005 | Belleguic et al. ....... | 156/64 |
| 2005/0191925 A1 | 9/2005 | Tilton et al. | |
| 2005/0279168 A1 * | 12/2005 | Bungenberg ........... | 73/571 |

FOREIGN PATENT DOCUMENTS

DE            3832431 A1 *   4/1990
WO      WO 01/37252 A2 *   5/2001

* cited by examiner

*Primary Examiner*—Hezron Williams
*Assistant Examiner*—Rose M Miller
(74) *Attorney, Agent, or Firm*—Brooks Kushman P.C.

(57) ABSTRACT

A method for measuring a first angular specific sound absorption spectrum of a first sound absorbing sample. The first sound absorbing sample has a predetermined random incidence sound absorption spectrum. The angular specific sound absorption spectrum is determined from a sound wave incident on a surface of the first sound absorbing sample with a predetermined angle of incidence that is greater than zero degrees from a plane parallel to the surface of the first surface. A first weighting factor that provides a fit of the angle specific sound absorption spectrum of the first sound absorbing sample to the predetermined random sound absorption spectrum is then determined. Next, a second angular specific sound absorption spectrum of a second sound absorbing sample at the predetermined angle of incidence is determined. The weighting factor is then used to determine the random specific sound absorption spectrum from the angle absorption spectrum of the second sound absorbing sample.

19 Claims, 2 Drawing Sheets

RANDOM INCIDENT ABSORBER APPROXIMATION

BACKGROUND OF THE INVENTION

1. Field of the Invention

The present inventions relates to methods of determining random sound absorption of materials and to an apparatus utilizing such methods.

2. Background Art

There is an increasing demand for the reduction of sound levels to improve perception in the passenger compartments of automobiles. Development of methods and systems that accomplish such reductions require an understanding of the potential internal and external noise sources in an automobile as well as the effect of various automobile components in masking or attenuating such noise. Moreover, reduction of noise in the 1 KHZ to 5 KHz frequency range is particularly desirable due to the increased sensitivity of vehicle passengers in that range for speech intelligibility and speech clarity.

Various testing methodologies are used to evaluate the sound absorbing properties that may be included in automobile applications. In particular, two test types are utilized by many automobile component suppliers. These two test types are provided by ASTM C384, ASTM E1050, and ASTM C423. The ASTM C384 and ASTM E1050 tests gives the sound absorption performance of a material by using sound waves that impinge perpendicular to the surface of a material being tested. The sound performance is evaluated from the measured absorption versus frequency plots determined in this method. FIG. 1 provides a schematic of an apparatus that is used to perform normal incidence sound absorption measurements in accordance with ASTM C384. Sound absorption apparatus 10 includes sound source 12 which forms a plane sound wave traveling along one direction 14 down tube 16. The sound wave is reflected back by test sample 18 to produce a standing wave. Test sample 18 is mounted on a sample holder 20. The induced standing wave is analyzed with one or more microphones 22, 24. The normal incidence sound absorption coefficient, $\alpha_n$, is determined from the standing wave ratio at face 24 of the test specimen. The impedance ratio, $z/\rho c$, is also found by measuring the position of the standing wave with reference to face 26 test sample 18.

ASTM C384 is capable of measuring small samples (on the order of 100 diameter) with a tabletop apparatus. Moreover, measures are performed quickly on the order of minutes. ASTM C423 on the other hand uses sound waves that impinge on a sample with a random angle of incidence. Again, absorption versus frequency plots are obtained by this methodology. However, it take several hours to perform the measurement of ASTM C423. Moreover, the equipment used for random incidence sound absorption is large. Typically, the chamber used in these methods are about 125 cu feet with 72 square feet in surface area of about 72 square feet. In addition, the test chamber needs to be a reverberant room. Also, adding the expense of the ASTM C423 method, multiple microphones or a traversing microphones are used. The material to be tested is often introduced in a manner that introduces edge effects that make the results somewhat not repeatable. Although the normal incidence method of determining sound absorption is quick and inexpensive, there is no clear way of predicting random incidence behavior from normal incidence data.

Accordingly, there exists a need for inexpensive simpler methods and apparatus for determining random incidence sound absorption.

SUMMARY OF THE INVENTION

The present invention solves one or more problems of the prior art by providing in at least one embodiment a method for predicting random incidence sound absorption of unknown sound absorbing samples. The method of this embodiment comprises measuring a first angular specific sound absorption spectrum of a first sound absorbing sample. The first sound absorbing sample has a predetermined random incidence sound absorption spectrum. The angular specific sound absorption spectrum is determined from a sound wave incident on a surface of the first sound absorbing sample with a predetermined angle of incidence that is greater than zero degrees from a plane parallel to the surface of the first surface. A first weighting factor that provides a fit of the angle specific sound absorption spectrum of the first sound absorbing sample to the predetermined random sound absorption spectrum is then determined. Next, a second angular specific sound absorption spectrum of a second sound absorbing sample at the predetermined angle of incidence is determined. The weighting factor is then used to determine the random specific sound absorption spectrum from the angle absorption spectrum of the second sound absorbing sample.

The present invention is advantageously used to screen material for automotive sound absorption characteristics. Once a suitable material is found, the random incidence test may be performed to confirm a material's suitability for such applications.

DETAILED DESCRIPTION OF THE PREFERRED EMBODIMENT(S)

Reference will now be made in detail to presently preferred compositions or embodiments and methods of the invention, which constitute the best modes of practicing the invention presently known to the inventors.

As used herein "sound absorption spectrum" means the plot of sound absorption versus sound frequency of a material.

As used herein "angular specific sound absorption spectrum" means the plot of sound absorption versus sound frequency of a material for sound waves incident on a sample at a set predetermined angle of incidence. For example, ASTM C384 provides the angular specific sound absorption spectrum for a normal angle of incidence (i.e., zero degrees).

In an embodiment of the present invention, a method for predicting random incidence sound absorption of an unknown sound absorbing sample is provided. The sound absorbing sample is an unknown sound absorbing sample in that its random incidence sound absorption spectrum is not known. The method of this embodiment comprises measuring a first angular specific sound absorption spectrum of a first sound absorbing sample. The first sound absorbing sample has a predetermined random incidence sound absorption spectrum. The angular specific sound absorption spectrum is determined from a sound wave incident on a surface of the first sound absorbing sample with a predetermined angle of incidence that is greater than zero degrees from a plane parallel to the surface of the first surface. A first weighting factor that provides a fit of the angle specific sound absorption spectrum of the first sound absorbing sample to the predetermined random sound absorption spectrum is then determined. Next, a second angular specific sound absorption spectrum of a second sound absorbing sample at the predetermined angle of incidence is determined. The weighting factor is then used to determine the random specific sound absorption spectrum from the angle absorption spectrum of the second sound absorbing sample.

In a variation of the present embodiment, the first and second angular sound absorption spectra are determined by methods analogous to the methods disclosed in ASTM C384-04 and ASTM E1050-98 except that the angle of incidence is adjusted to an angle different than normal incidence. The entire disclosures of ASTM C384-04 and ASTM E1050-98 are hereby incorporated by reference. In general, the first and second angular absorption spectra are determined by directing the sound wave onto a first oblique section of the first sound absorbing sample or a second oblique section of the second sound absorbing sample. In a refinement of the present variation, the first oblique section or the second oblique section is mounted on a wedge-shaped metal sample holder placed within a cylindrical tube that is used in an apparatus that executes the methods of the invention.

Figure 1:
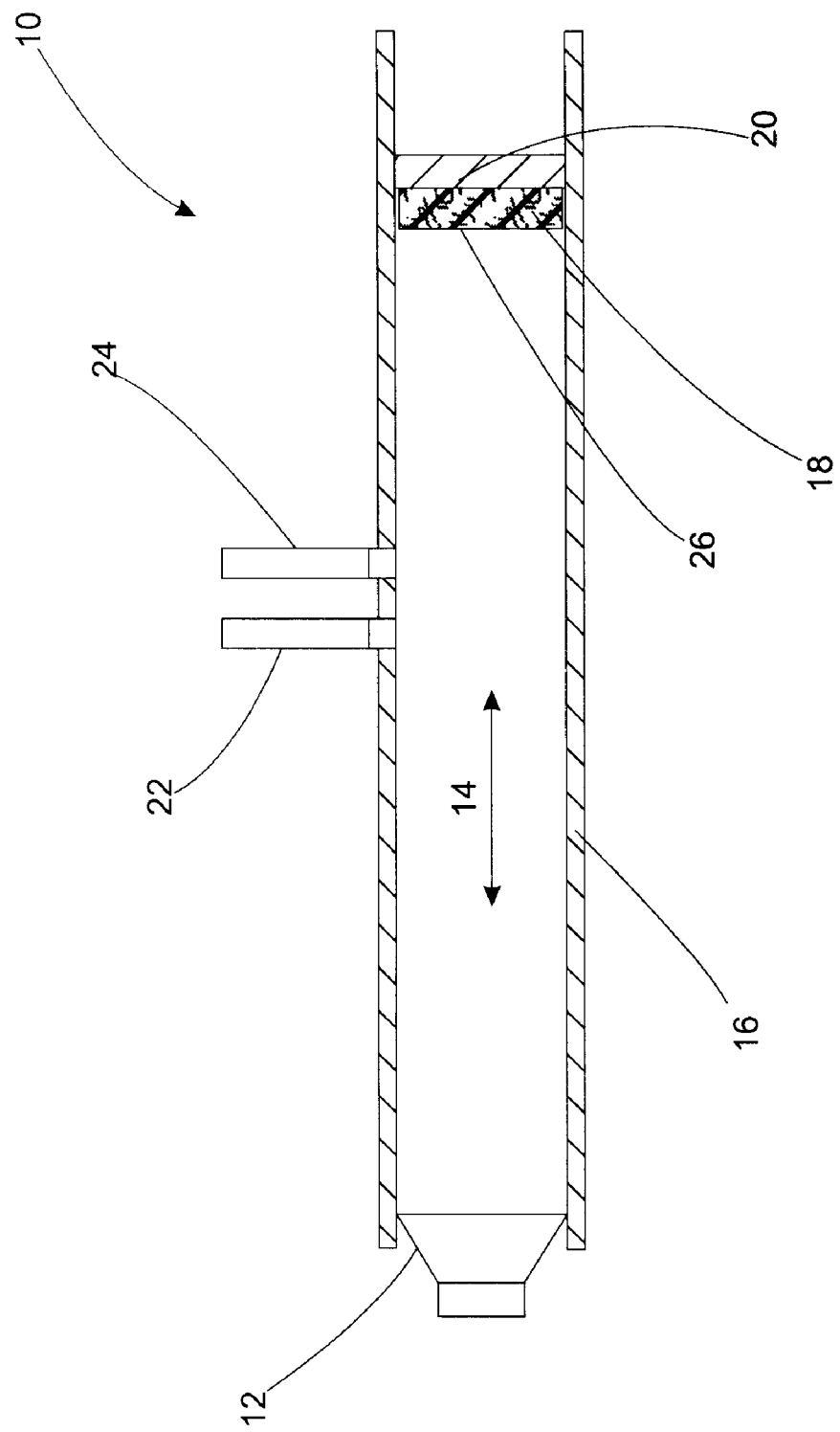
FIG. 1 is a schematic of an apparatus for measuring sound absorption at normal incidence.
Figure 2:
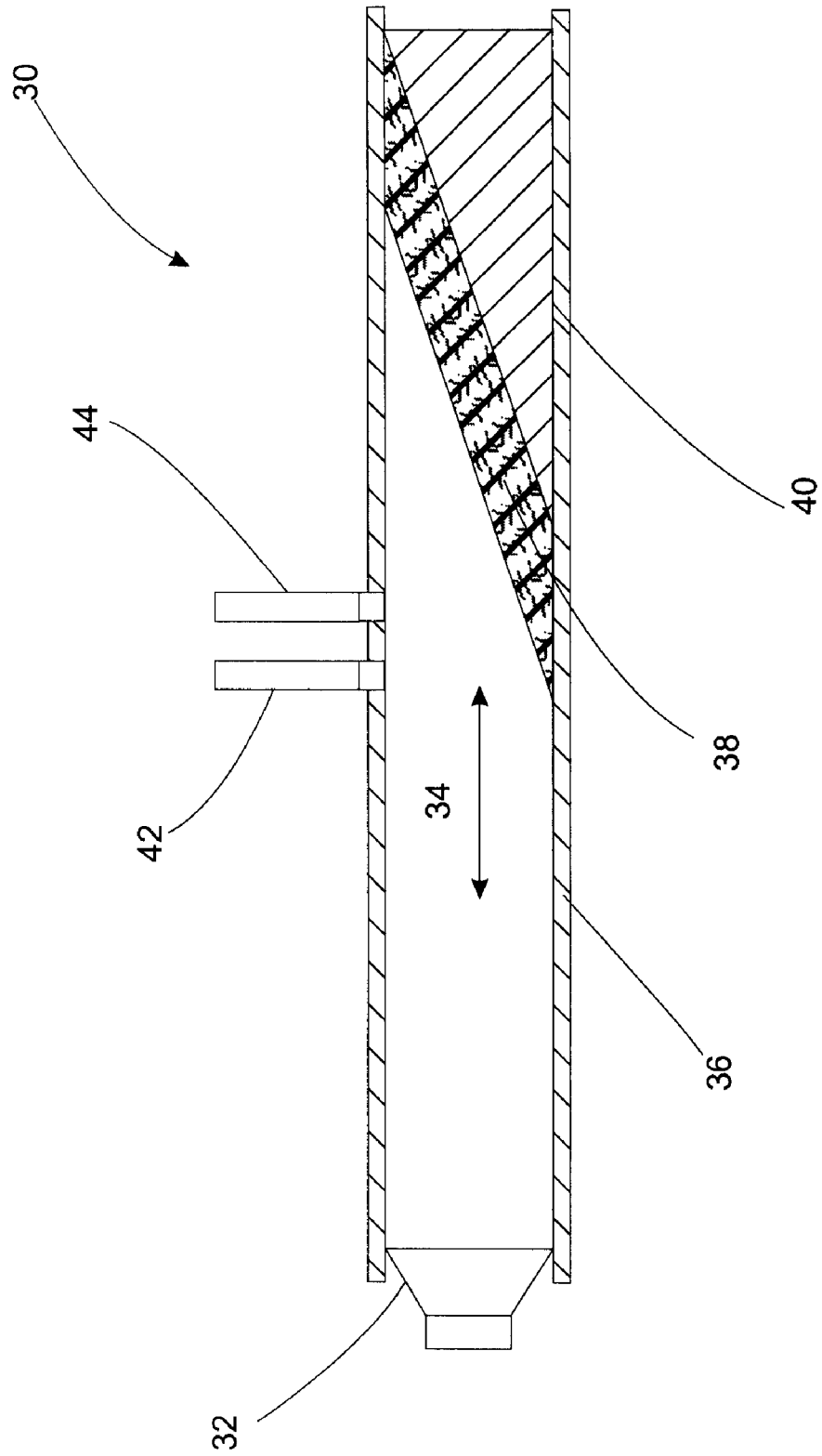
FIG. 2 is a schematic of an apparatus for measuring sound absorption at varying angles of incidence.

With reference to FIG. 2, a schematic of an apparatus that is used to perform sound absorption measurements at varying angles is provided. Sound absorption apparatus 30 includes sound source 32 which forms a plane sound wave traveling along one direction 34 down tube 36. The sound wave is reflected back by test sample 38 to produce a standing wave. Test sample 38 is mounted on a sample holder 40. The induced standing wave is analyzed with one or more microphones 42, 44. When a method employing the sound absorption techniques of ASTM C384-04 is used, sound source 32 generates pure tones and the sound absorption coefficient, $\alpha_n$, at a predetermined angle of incidence is determined from the standing wave ratio at face 44 of the test specimen. Since test sample 38 may be angled relative to the impinging sound waves, the position of the standing wave ratio used in the calculation of $\alpha_n$ is any position on face 44. In a variation, this position is the center of face 44. When a method employing the sound techniques of ASTM E1050-98 are used, plane waves are generated in the tube using a broad band signal from sound source 32 with decomposition of the stationary sound wave pattern into forward- and backward-traveling components being achieved by simultaneously measuring sound pressures at two spaced locations from microphones 42, 44. Calculations of the normal incidence absorption coefficient, $\alpha_n$, is accomplished processing an array of complex data from a measured transfer function. Typically, the angle of incidence of the present embodiment is greater than zero degrees. In a variation, the angle of incidence is from about 10 to about 80 degrees. In another variation, the angle of incidence is from about 30 to about 60 degrees.

The weighting factor used in the present embodiment, is determined to give the best fit between the first angular specific sound absorption spectrum to the known random incidence absorption spectrum of the first sound absorbing sample. For example, the weight factor w is determined such that wF(v) gives the best least square estimate of R(v) where F(v) represents the angular specific sound absorption of the first sample, R(v) represents known random incidence sound absorption of the first sample. The known random incidence sound absorption spectrum is determined in accordance to the method of ASTM C423-029 or any other method capable of determining this spectrum. The entire disclosure of ASTM C423-02a is hereby incorporated by reference.

In another embodiment of the present invention, a method predicting random incidence sound absorption of unknown sound absorbing sound absorbing sample is provided. The method of the present embodiment is an extension of the methods set forth in the embodiments and variations set forth above except that two or more angular specific absorption spectra are determined. The method of this embodiment comprises measuring a first plurality of angular specific sound absorption spectra for a first sound absorbing sample. As set forth above, the angular specific absorption spectra are determined by a sound wave incident on a surface of the first sound absorbing sample with a corresponding plurality of predetermined angles of incidence wherein the first sound absorbing sample has a predetermined random incidence sound absorption spectrum. Next, a plurality of weighting factors that provides a fit of the angle specific sound absorption spectra of the first sound absorbing sample to the predetermined random sound absorption spectrum are determined. A second plurality of angular specific sound absorption spectra of a second sound absorbing sample are then measured at the predetermined angles of incidence. Finally, the plurality of weighting factors are used to determine the random specific sound absorption spectrum from the angle absorption spectra of the second sound absorbing sample.

In a variation of the present embodiment, the first and second plurality of angular specific sound absorption spectra are determined by methods analogous to the methods disclosed in ASTM C384-04 and ASTM E1050-98 except that spectra at more than one angle of incidence are determined. Typically, at least one angle of incidence in the plurality of predetermined angles of incidence is used. In a variation, the plurality of predetermined angles of incidence include angles from about 10 to about 80 degrees. In another variation, the angle of incidence is from about 30 to about 60 degrees. In general, the first and second angular absorption spectra are determined by directing the sound wave onto a first oblique section of the first sound absorbing sample or a second an oblique section of the second sound absorbing sample. In a refinement of the present variation, the first oblique section or the second oblique section is mounted on a wedge-shaped metal sample holder place within a cylindrical tube that is used in an apparatus that executes the methods of the invention.

The plurality of weighting factors used in the present embodiment, is determined to give the best fit between the first angular specific sound absorption spectrum to the known random incidence absorption spectrum of the first sound absorbing sample. For example, the weight factors $w_i$ is determined such that the sum of $w_i F_i(v)$ gives the best least square estimate of R(v) where $F_i(v)$ represents a spectrum of the plurality of angular specific sound absorption spectra of the first sample, R(v) represents the known random incidence sound absorption of the first sample. The known random incidence sound absorption spectrum is determined in accordance to the method of ASTM C423-02a or any other method capable of determining this spectrum.

In a variation of the present embodiment, the angular sound absorption spectra are determined by methods analogous to the methods disclosed in ASTM C384-04 and ASTM E1050-98 except that the angle of incidence is adjusted to include at least one angle that is different than normal incidence. The first and second plurality of angular sound absorption spectra are determined by directing the sound wave onto a first oblique section of the first sound absorbing sample or a second oblique section of the second sound absorbing sample. The first and second oblique sections are at such angles to provide the required angle of incidence. In one variation, the first oblique section or the second oblique section is mounted on a wedge-shaped metal sample holder place within a cylindrical tube. For example, a series of oblique section s of the first sound absorbing spectra having an angle of incidence of 0, 30, 45, and 60 degrees provide a set of four sound absorption spectra. These four sound absorption spectra are then linearly combined with four weighting factors that are a best fit (i.e., a least squares fit) to the know random incidence spectra of the first sample. Take a known sample, the weighting factors inherent in process not material.

In another embodiment of the invention, a method predicting random incidence sound absorption of an unknown sound absorbing sample is provided. In the present embodiment one or more angular specific sound absorption spectra for oblique sectioned sample. The method of the present embodiment comprises measuring one or more angular specific sound absorption spectra for a first oblique sectioned sample. Again, the one or more angular specific sound absorption spectra are determined by a sound wave incident on a surface of the first oblique sectioned sound absorbing sample with corresponding one or more predetermined angles of incidence. The first oblique section ed sound absorbing sample has a predetermined random incidence sound absorption spectrum. One or more weighting factors that provides a fit of the angle specific sound absorption spectra of the first oblique sectioned sound absorbing sample to the predetermined random sound absorption spectrum are then determined. Next, one or more angular specific sound absorption spectra of a second oblique sectioned sound absorbing sample at the predetermined angles of incidence are measured. The one or more weighting factors are used to determine the random specific sound absorption spectrum from the angle absorption spectra of the second oblique sectioned sound absorbing sample.

In a variation of the present embodiment, the one or more angular specific sound absorption spectra are determined by methods analogous to the methods disclosed in ASTM C384-04 and ASTM E1050-98 except that spectra at least one angle of incidence greater than zero degrees is used. In a variation, the one or more predetermined angles of incidence include angles from about 10 to about 80 degrees. In another variation, the one or more predetermined angles of incidence include angles from about 30 to about 60 degrees. In general, the first and second angular absorption spectra are determined by directing the sound wave onto a first oblique section of the first sound absorbing sample or a second oblique section of the second sound absorbing sample. In a refinement of the present variation, the first oblique section or the second oblique section is mounted on a wedge-shaped metal sample holder place within a cylindrical tube that is used in an apparatus that executes the methods of the invention.

The one or more weighting factors used in the present embodiment, is determined to give the best fit between the first angular specific sound absorption spectrum to the known random incidence absorption spectrum of the first sound absorbing sample. For example, the weight factors $w_i$ is determined such that the sum of $w_i F_i(v)$ gives the best least square estimate of $R(v)$ where $F_i(v)$ represents a spectrum of the plurality of angular specific sound absorption spectra of the first sample, $R(v)$ represents the known random incidence sound absorption of the first sample. The know random incidence sound absorption spectrum is determined in accordance to the method of ASTM C423-302a or any other method capable of determining this spectrum.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A method predicting random incidence sound absorption and unknown sound absorbing sample, the method comprising:
    a) measuring a first angular specific sound absorption spectrum of a first sound absorbing sample, the angular specific sound absorption spectrum being determined a sound wave incident on a surface of the first sound absorbing sample with a predetermined angle of incidence greater than zero degrees from a plane parallel to the surface of the first surface wherein the first sound absorbing sample has a predetermined random incidence sound absorption spectrum;
    b) determining a first weighting factor that provides a fit of the angle specific sound absorption spectrum of the first sound absorbing sample to the predetermined random sound absorption spectrum;
    c) measuring a second angular specific sound absorption spectrum of a second sound absorbing sample at the predetermined angle of incidence; and
    d) using the first weighting factor from step c) to determine the random specific sound absorption spectrum from the angle absorption spectrum of the second sound absorbing sample.

2. The method of claim 1 wherein first and second angular sound absorption spectra are determined by directing the sound wave onto a first oblique section of the first sound absorbing sample or a second oblique section of the second sound absorbing sample.

3. The method of claim 2 wherein first oblique section or the second oblique section is mounted on a wedge-shaped metal sample holder placed within a cylindrical tube.

4. The method of claim 1 wherein first and second angular sound absorption spectrums are measured in accordance with ASTM C384-04 or ASTM E1050-98 except for the angle of incidence being greater than zero degrees.

5. The method of claim 1 wherein the angle of incidence is from about 10 to about 80 degrees.

6. The method of claim 1 wherein the angle of incidence is from about 30 to about 60 degrees.

7. A method predicting random incidence sound absorption and unknown sound absorbing sample, the method comprising:
    a) measuring a first plurality of angular specific sound absorption spectra for a first sample, the plurality of angular specific sound absorption spectra being determined by a sound wave incident on a surface of the first sound absorbing sample with corresponding plurality of predetermined angles of incidence wherein the first sound absorbing sample has a predetermined random incidence sound absorption spectrum;
    b) determining a plurality of weighting factors that provides a fit of the angle specific sound absorption spectra of the first sound absorbing sample to the predetermined random sound absorption spectrum;
    c) measuring a second plurality of angular specific sound absorption spectra of a second sound absorbing sample at the predetermined angles of incidence; and
    d) using the plurality of weighting factors from step c) to determine the random specific sound absorption spectrum from the angle absorption spectra of the second sound absorbing sample.

8. The method of claim 7 wherein the plurality of weighting factors are determined by a least squares fit of the first plurality of angular specific sound absorption spectra to the predetermined random sound absorption spectrum.

9. The method of claim 7 wherein first and second plurality of angular sound absorption spectra are determined by directing the sound wave onto a first oblique section of the first sound absorbing sample or a second oblique section of the second sound absorbing sample.

10. The method of claim 9 wherein a first oblique section or a second oblique section is mounted on a wedge-shaped metal sample holder place within a cylindrical tube.

11. The method of claim 10 wherein first and second angular sound absorption spectrums are measured in accordance with ASTM C384-04 or ASTM E1050-98 except for the angle of incidence being greater than zero degrees.

12. The method of claim 7 wherein the angle of incidence is from about 10 to about 80 degrees.

13. The method of claim 7 wherein the angle of incidence is from about 30 to about 60 degrees.

14. A method predicting random incidence sound absorption and unknown sound absorbing sample, the method comprising:
   a) measuring one or more angular specific sound absorption spectra for a first oblique sectioned sample, the one or more angular specific sound absorption spectra being determined by a sound wave incident on a surface of the first oblique sectioned sound absorbing sample with corresponding one or more predetermined angles of incidence wherein the first oblique sectioned sound absorbing sample has a predetermined random incidence sound absorption spectrum;
   b) determining one or more weighting factors that provides a fit of the angle specific sound absorption spectra of the first oblique sectioned sound absorbing sample to the predetermined random sound absorption spectrum;
   c) measuring one or more angular specific sound absorption spectra of a second oblique sectioned sound absorbing sample at predetermined angles of incidence; and
   d) using the one or more weighting factors from step c) to determine the random specific sound absorption spectrum from the angle absorption spectra of the second oblique sectioned sound absorbing sample.

15. The method of claim 14 wherein the one or more weighting factors are determined by a least squares fit of the one or more angular specific sound absorption spectra to the predetermined random sound absorption spectrum.

16. The method of claim 14 wherein the first oblique sectioned sample and the oblique sectioned sample are mounted on a oblique sectioned metal sample holder placed within a cylindrical tube.

17. The method of claim 14 wherein first and second angular sound absorption spectrums are measured in accordance with ASTM C384-04 or ASTM E1050-98 except for the angle of incidence being greater than zero degrees.

18. The method of claim 14 wherein the angle of incidence is from about 10 to about 80 degrees.

19. The method of claim 14 wherein the angle of incidence is from about 30 to about 60 degrees.

* * * * *